United States Patent [19]

Pepper

[11] Patent Number: 4,457,327
[45] Date of Patent: Jul. 3, 1984

[54] TEMPERATURE RESPONSIVE VALVE MECHANISM

[75] Inventor: Kenneth V. Pepper, Elkhart Lake, Wis.

[73] Assignee: Bemis Manufacturing Company, Sheboygan Falls, Wis.

[21] Appl. No.: 402,081

[22] Filed: Jul. 26, 1982

[51] Int. Cl.$^3$ ............................................... F16K 7/12
[52] U.S. Cl. ..................... 137/67; 206/438; 220/201; 220/202; 220/209; 422/112; 422/113; 422/114; 422/310
[58] Field of Search ................ 422/26, 112, 113, 114, 422/295, 310; 206/213.1, 370, 438, 524.8; 220/202, 209, 361, 201; 137/72, 73, 468, 67

[56] References Cited

U.S. PATENT DOCUMENTS

| | | | |
|---|---|---|---|
| 1,960,271 | 5/1934 | Lovekin | 137/73 |
| 2,097,585 | 11/1937 | Carson | 137/468 |
| 2,688,975 | 9/1954 | Born | 137/73 |
| 2,760,343 | 8/1956 | Reed | 137/14 |
| 3,651,823 | 3/1972 | Milstead, Sr. | 137/72 |
| 3,687,290 | 8/1972 | Myers | 210/149 |
| 3,730,205 | 5/1973 | Guimbellot | 137/73 |
| 3,949,934 | 4/1976 | Goglio | 220/209 X |
| 4,143,670 | 3/1979 | Olson et al. | 137/72 |
| 4,193,416 | 3/1980 | Slawson | 137/72 X |
| 4,196,166 | 4/1980 | Sanderson et al. | 22/33 |
| 4,221,231 | 9/1980 | Harvey et al. | 137/72 |
| 4,228,914 | 10/1980 | Sanderson | 422/112 X |
| 4,247,517 | 1/1981 | Sanderson et al. | 422/112 X |
| 4,251,482 | 2/1981 | Sanderson et al. | 422/26 |
| 4,273,251 | 6/1981 | McMahon | 220/361 |
| 4,349,118 | 9/1982 | Sanderson et al. | 422/26 X |

FOREIGN PATENT DOCUMENTS 0475769 8/1951 Canada ................................. 137/72

Primary Examiner—Barry S. Richman
Assistant Examiner—Brion P. Heaney
Attorney, Agent, or Firm—Dressler, Goldsmith, Shore, Sutker & Milnamow, Ltd.

[57] ABSTRACT

A unique temperature responsive operating mechanism is disclosed which is particularly suited for embodiment as a temperature responsive valve mechanism for use with a steam sterilization container. The mechanism includes a valve operating member which is movable by the action of a biasing spring from a first, opened position to a second, closed position with respect to an opening defined by the sterilization container. The mechanism further includes a temperature responsive, heat deformable member operatively associated with the biasing spring and the valve operating member to provide progressive movement of the valve operating member from its first to its second position in response to an elevation in temperature of the environment of the operating mechanism. Desired communication is provided between the interior and exterior of the sterilization container during a substantial portion of the steam sterilization process, with the mechanism subsequently tightly sealing the container. The mechanism further functions in the nature of one-way valve to permit escape of vapor pressure from the sterilization container to assure that the contents therein are properly dried during the vacuum drying cycle of the steam sterilization process.

26 Claims, 9 Drawing Figures

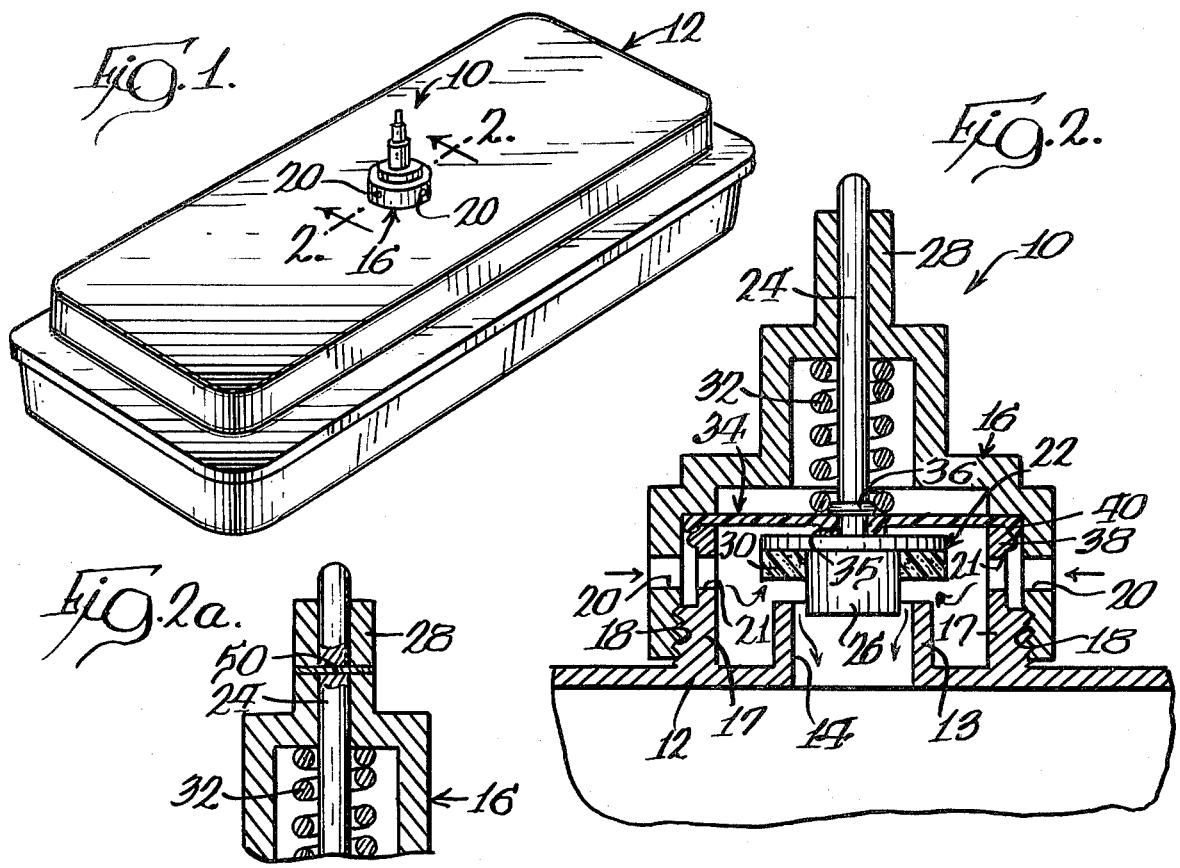
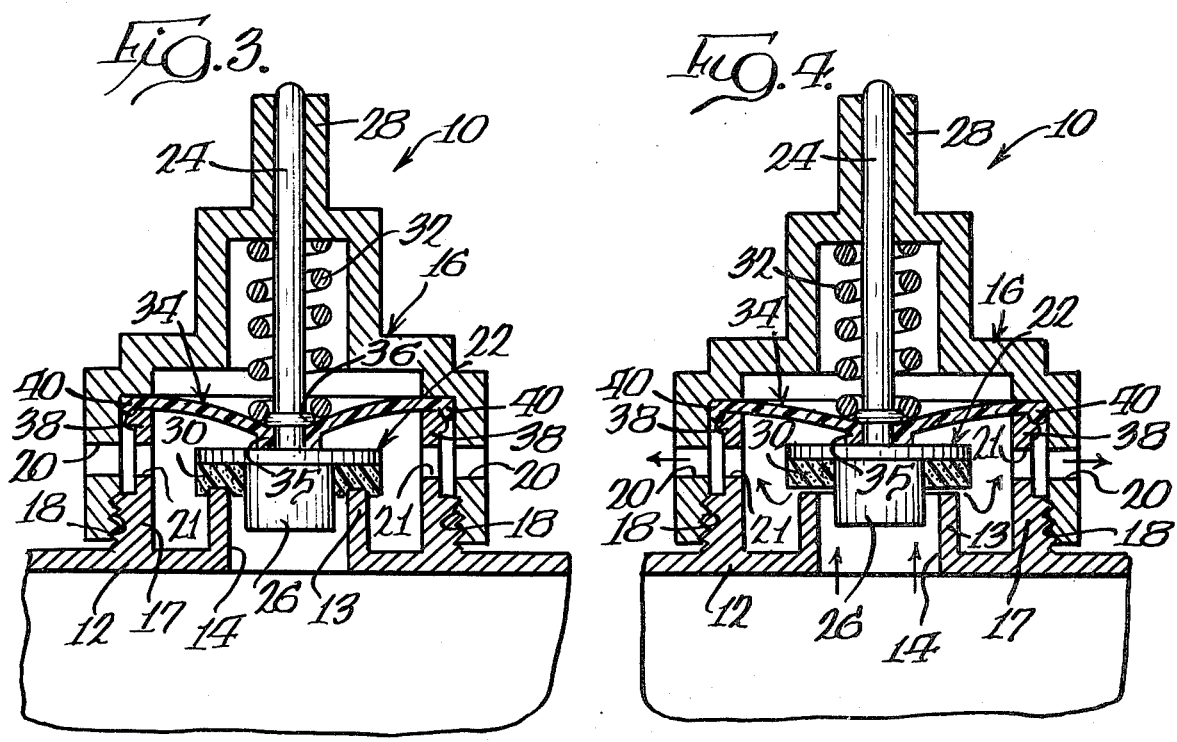

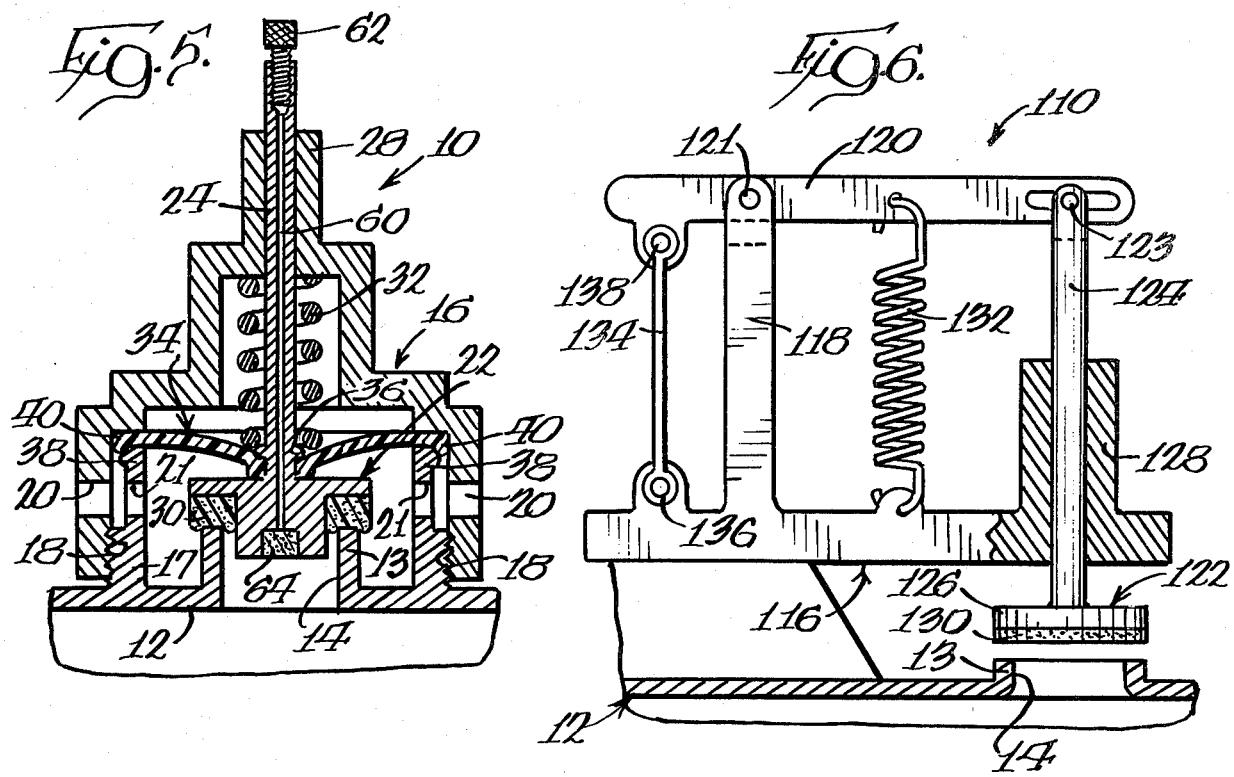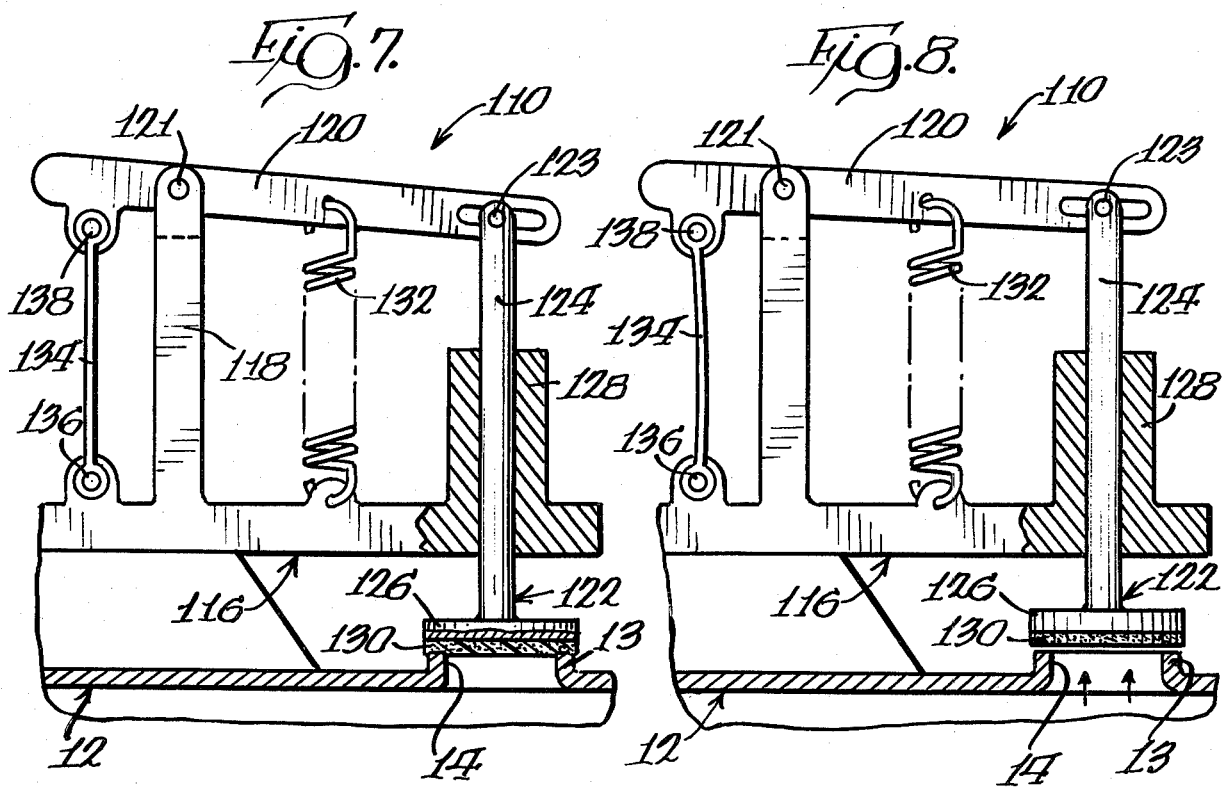

TEMPERATURE RESPONSIVE VALVE MECHANISM

TECHNICAL FIELD

The present invention relates generally to temperature responsive devices, and more particularly to a temperature responsive operating mechanism which is particularly suited for use as a valve operating mechanism for a container used for steam sterilizing medical instruments and the like.

BACKGROUND OF THE INVENTION

Sterilization of a large number of medical instruments and like articles must be routinely performed in health care facilities. In the past, instruments to be sterilized have typically been cleaned and wrapped in cloth or cloth-like materials prior to placement on trays for subsequent sterilization in a specially constructed steam sterilization chamber. Following sterilization, the sealed packages of instruments are stored in a "clean room" where they are considered to remain sterile for a limited and accepted period of time. Procedures such as this have been regarded as providing adequate protection against contamination for several decades.

Because of the large number of articles which must be routinely sterilized, attempts have been made to improve the efficiency of the sterilization procedure. Because the above-described wrapping technique for sterilization is both material intensive and time-consuming, sealable metal containers have been introduced for holding unwrapped instruments for sterilization and subsequent storage. However, use of such sterilization containers presents special problems which relate to the nature of the typical steam sterilization process.

During steam sterilization, articles within a sterilization chamber (an autoclave) are subjected to several distinct operational cycles. After articles to be sterilized are placed in the chamber and the chamber sealed, air is evacuated from the chamber to a desired level of vacuum, with negative pressure being maintained for aproximately one minute duration. At the conclusion of this first vacuum cycle, steam is admitted to the chamber and the temperature within the chamber is elevated, such as to a temperature on the order of approximately 270 degrees Fahrenheit. The articles in the chamber are typically subjected to this elevation in temperature for approximately six minutes. At the conclusion of this steam sterilization cycle, the supply of hot steam is turned off, and a vacuum drying cycle commenced. The vacuum applied to the chamber drives off the residual water from the steam, with the elevation of the temperature within the chamber during this vacuum drying cycle thoroughly drying the articles being sterilized. The temperature within the sterilization chamber during this second vacuum cycle is typically on the order of 270 degrees Fahrenheit, with the articles in the chamber being subjected to vacuum drying for approximately one hour. Sterilization is then complete, and the articles can be removed from the sterilization chamber for subsequent storage and use.

In order to assure proper sterilization of articles, metal containers for holding the articles during sterilization must be adapted to permit free flow of hot steam into and from the container during the steam cycle, and subsequent evacuation of air and moisture from the container during the vacuum drying cycle. In order to facilitate convenient handling and storage of the instruments after sterilization, the sterilization container is preferably arranged so that it is completely sealed against contamination at the conclusion of the sterilization process.

In the past, some metal sterilization containers have included membrane-like filters permeable to air and moisture, but impenetrable to undesired organisms and like contaminants. Such filters permit the desired communication with the interior of the container during the sterilization process. However, these types of filters must be properly fitted in order to be effective, and have proven to be prone to damage and improper installation. Additionally, such permeable filters provide no indication that the integrity of their seal has not been violated.

In view of this, it is desirable that a metal sterilization container be vacuum sealed at an appropriate point in the sterilization process in a manner which maintains the vacuum of the container during post-sterilization storage. The presence of the vacuum in the sealed container can be readily detected by an appropriate vacuum gauge on the container, and by the force required to break the vacuum accompanied by the audible inrush of air. A mechanism for sealing the sterilization container in this manner must function reliably and predictably, and must be sufficiently economical to use.

Thus, it is desirable that some type of valve mechanism be provided for the sterilization container to permit the desired communication between the interior and exterior of the container during sterilization, but which acts to permit vacuum sealing of the container against contamination at the conclusion of sterilization. Such a mechanism should preferably be relatively inexpensive and easy to use, and function predictably to assure proper sterilization of the articles. Because efficient sterilization of medical articles helps to hold down the increasing cost of health care, the introduction of an easily used, temperature responsive valve operating mechanism for sterilization containers which is economical and reliable is particularly desirable.

SUMMARY OF THE INVENTION

In accordance with the present invention, a temperature responsive operating mechanism is disclosed which is particularly suited for embodiment as a valve operating mechanism for a steam sterilization container. When used in conjunction with a sterilization container, the operating mechanism functions to slowly close the valve and thereby permit communication between the interior and exterior of the container during a substantial portion of the sterilization process. The operating mechanism further functions to permit evacuation of air and moisture from the container during the vacuum drying cycle, and automatically vacuum seals the container against contamination when sterilization is complete so that the container and its sterilized contents may be easily handled and stored. The operating mechanism is structured so that a clear visual indication is provided that sterilization is complete, further facilitating efficient handling of the sterilized articles.

While the present operating mechanism is disclosed in association with a sterilization container, it will be apparent that the mechanism can be readily adapted for a wide variety of applications where temperature responsive actuation of an operating member is desired. For example, the present operating mechanism may be used for protection of electrical wiring, as an electrical switching device, or as a fire detection apparatus. Other applications will be readily apparent, particularly in view of the straightforward and inexpensive construction of the mechanism, and the readily predictable and repeatable functioning of the device.

When embodied as a valve operating mechanism for a sterilization container, the present mechanism comprises a suitable housing or like support structure which is adapted for mounting on the sterilization container in association with an opening typically defined by the container to provide communication between the interior and the exterior of the container. The operating mechanism further includes a valve operating member which is supported by the support structure for movement from a first, opened position wherein the container opening is unsealed by the valve member, to a second, closed position wherein the valve member seals and closes the container opening.

The present operating mechanism further includes temperature responsive operating means for controlling the movement of the valve operating member from its first, opened position to its second, closed position responsive to an elevation in the temperature of the environment of the mechanism. During steam sterilization, the environment of the mechanism is the interior of the sterilization chamber.

The temperature responsive operating means comprises a biasing arrangement, such as a biasing spring, operatively associated with the support structure of the mechanism and the valve operating member for urging the valve member from its first position toward its second position. The operating means further include a disposable heat deformable member operatively associated with the biasing spring and the valve operating member for opposing the biasing action of the biasing spring on the operating member. The heat deformable member is arranged so that it deforms in response to elevation in temperature whereby the biasing spring progressively moves the valve operating member from its first position to its second position in a controlled and predictable fashion. In this manner, the operating mechanism functions to seal the opening in the sterilization container during the temperature elevation of the sterilization process, preferably during the vacuum drying cycle.

Significantly, the heat deformable member of the present invention functions in a unique fashion by taking advantage of the tendency of materials to "creep", i.e., non-elastically deform when subjected to stresses below their yield point, at temperatures below the melting points of the materials. In the present invention, the heat deformable member preferably comprises a thermoplastic material which is non-elastically deformable when subjected to stresses by the biasing spring of the mechanism below the non-elastic yield stress of the material at temperatures below the melting point of the material. While the tendency of materials to creep is usually considered a disadvantageous property that imposes limits on the load to which the material may be subjected, or limits the temperature at which they can be usefully employed, this very property is exploited in the present invention. By appropriately fabricating the heat deformable member, the member resists the action of the biasing spring on the valve operating member of the mechanism at room temperatures, but begins to creep when subjected to elevated temperatures, such as during sterilization. In this manner, readily predictable and controlled movement of the valve operating member is provided so that it moves to close the opening in the sterilization container after a predetermined period in the sterilization process. Thus, desired communication is provided between the interior and exterior of the sterilization container.

Notably, the present operating mechanism is arranged to permit deformation of the heat deformable member to permit movement of the valve operating member from its second, closed position toward its first position in opposition to the biasing spring, even at non-elevated temperatures. This a particularly important feature of the present mechanism when used in conjunction with a sterilization container, since this action permits the valve mechanism to open in response to a pressure differential between the interior and exterior of the container. In this way, vapor is evacuated from the container during the vacuum drying cycle of the sterilization process, with mechanism functioning in the nature of a one-way valve. When the sterilization process is complete, the biasing spring of the mechanism immediately urges the valve operating member into its second, closed position so that the articles within the evacuated sterilization container remain uncontaminated, and the container can be easily handled and stored.

In one embodiment of the present invention, the support structure of the mechanism comprises the housing which is adapted to be removably fitted to the sterilization container about the opening therein. The housing supports the valve operating member for reciprocable movement within the housing. The heat deformable member of the mechanism preferably comprises a disc-like diaphram which extends between the valve member and the housing. The biasing spring comprises a compression coil spring disposed on an elongated stem portion of the valve member, with the spring held captive between the heat deformable member and the housing.

In another embodiment, the support structure of the mechanism includes a support strut which pivotally supports an operating lever. The lever includes a portion operatively connected with a reciprocably movable valve operating member supported by the support structure. A biasing spring extends between and is operatively connected with the lever and the support structure for urging the valve member from its first, open position with respect to the opening in the sterilization container, toward its second closed position. The heat deformable member of this embodiment preferably comprises an elongate member which extends between and is operatively connected with the support structure of the mechanism and the fulcrummed lever.

In either embodiment of the present invention, a suitable releasable connection comprising a fusible link can be provided operatively associated with the valve operating member of the mechanism for preventing unintended or premature movement of the valve member below a predetermined temperature. Either embodiment of the present invention may also be provided with a suitable venting arrangement which facilitates the equalization of pressure in the evacuated sterilization container when it is desired to open the container for use of the articles therein. To facilitate economical use of the present invention, the heat deformable member of the mechanism can be easily and inexpensively replaced, and the entire mechanism reused.

Numerous other advantages and features of the present invention will become readily apparent from the following detailed description of the invention and embodiments thereof, from the claims, and from the accompanying drawings in which like numerals are employed to designate like parts throughout the same.

BRIEF DESCRIPTION OF THE DRAWINGS

FIG. 1 is a perspective view of a sterilization container having the temperature responsive valve operating mechanism of the present invention mounted thereon;

FIG. 2 is a side elevational view in partial cross-section taken along lines 2—2 of FIG. 1 illustrating the present valve operating mechanism in an opened position;

FIG. 2A is a fragmentary view similar to the FIG. 2 illustrating a modification of the present valve operating mechanism;

FIG. 3 is a side-elevational view similar to FIG. 2 illustrating the present valve operating mechanism in a closed position;

FIG. 4 is a side elevational view similar to FIG. 3 illustrating the further operation of the present valve operating mechanism;

FIG. 5 is a side-elevational view in partial cross-section similar to FIGS. 2-4 illustrating a further modification of the present valve operating mechanism;

FIG. 6 is a side elevational view in partial cross-section illustrating an alternate embodiment of a valve operating mechanism in accordance with present invention in an opened position;

FIG. 7 is a view similar to FIG. 6 illustrating the alternate embodiment of the present valve operating mechanism in a closed position; and FIG. 8 is a view similar to FIG. 7 illustrating the further operation of the alternate embodiment of the present valve operating mechanism.

DETAILED DESCRIPTION OF THE DRAWINGS

The present invention is susceptible to embodiment in various forms, which are shown in the drawings. The various embodiments of the invention will herein after be described with the understanding that the present disclosure is to be considered as an exemplification of the invention and is not intended to limit the invention to the specific embodiments illustrated.

With reference now to FIGS. 1 and 2, therein is illustrated the temperature responsive valve operating mechanism 10 embodying the present invention shown mounted to a steam sterilization container 12. Container 12 is intended as illustrative, typically including upper and lower portions which may be suitably, sealingly joined after medical articles or the like to be sterilized have been placed therein. The entire container 12 and its contents may then be placed within a steam sterilization unit, commonly referred to as an autoclave, and the steam sterilization process commenced.

In order to permit sterilization and subsequent storage of sterilized articles, the construction of container 12 should be provided such that the container is capable of withstanding the stresses generated when sealed under internal vacuum for prolonged periods. Containers meeting these requirements can be readily fabricated from suitably corrosion and temperature resistant materials, with means provided for detachably mounting the present valve mechanism to the containers. For example, container 12 can be fabricated from suitable metallic materials, such as stainless steel. Alternately, containers such as 12 can be molded from high strength, high heat distortion temperature thermoplastics. For example, ULTEM polyethermide resin, marketed by the General Electric Company, or UDEL polysulfone resin, available from Union Carbide, as well as like plastic materials, can be used for manufacture of suitable sterilization containers. The advantages of fabricating sterilization containers from such plastic materials include economical manufacture of suitably temperature and stress resistant containers which can be essentially clear or transparent. This desirably permits visual inspection of the contents of a container prior to breaking the vacuum seal of the container for use of its contents.

In order to accommodate communication between the interior and exterior of the container 12, a projecting valve seat portion 13 of the container defines at least one opening 14. The valve mechanism 10 is positioned on container 12 in association with container opening 14 and functions to permit flow of hot steam through the opening during the steam sterilization cycle of the sterilization process, and further functions to permit evacuation of air and moisture from the container 12 during the vacuum drying cycle of the sterilization process.

In this embodiment of the present invention, valve mechanism 10 includes a support structure comprising housing 16 which is adapted to be removably mounted on container 12 so that the valve mechanism 10 fits about container opening 14. To this end, container 12 may include an upstanding shoulder portion 17 adapted for preferably detachable connection of housing 16 thereon, such as by thread connection 18. As will be appreciated, other types of quickly detachable connections may be provided for mounting housing 16 on shoulder portion 17, such as a bayonet connection for example. Valve housing 16 of the valve mechanism 10 is preferably fabricated from a material which is suitably temperature resistant to permit repeated use of the valve housing.

In order to further accommodate communication between the interior and exterior of sterilization container 12, valve housing 16 defines at least one passage 20 which provides communication between the interior and exterior of the valve housing. Communication is further accommodated by the provision of at least one passage 21 defined by shoulder portion 17 of the container 12, with passages 20 in housing 16 preferably generally aligned with the passages 21 defined by shoulder portion 17. Thus, communication between the interior and exterior of container 12 is provided via container opening 14, passages 21 in shoulder portion 17, and passages 20 in valve housing 16.

Valve mechanism 10 further includes a valve operating member 22 operatively associated with and supported by valve housing 16. In this embodiment, valve member 22 is reciprocably disposed within valve housing 16 for movement from a first, opened position with respect to container opening 14, to a second, closed position with respect to the container opening wherein valve member 22 seals and closes the opening. In FIG. 2, valve member 22 is illustrated in its first, opened position. As will be further described, FIG. 3 illustrates valve member 22 in its second, closed position with respect to the container opening 14.

Valve member 22 is preferably fabricated from the material which is suitably temperature resistant to permit reuse of the valve member. The valve member includes an elongate stem portion 24 and a head portion 26 connected to the stem portion. Guided reciprocable movement of the valve member within valve housing 16 is provided by guide portion 28 of the housing which engages stem portion 24 of valve member 22 for guiding the movement of the valve member. Head portion 26 of the valve member is adapted to sealingly engage valve seat 13 of container 12 which defines container opening 14 to tightly seal the container opening at appropriate times in the sterilization process. To this end, head portion 26 is provided with a sealing head gasket 30 fabricated from a elastomeric material so that head portion 26 of valve member 22 is adapted to sealingly close the container opening with an air tight, contaminant-proof seal when the valve member 22 is in its second, closed position.

In order to bias the valve member 22 from its first, opened position toward its second, closed position with respect to the container opening 14, valve mechanism 10 includes a biasing spring 32 operatively associated with valve housing 16 and the valve member 22. In this embodiment, the biasing spring 32 comprises a compression coil spring disposed about stem portion 24 of valve member 22.

In order to oppose the biasing action of spring 32 on the valve member 22 to prevent movement of the valve member to its second, closed position before a predetermined point in the sterilization process, valve mechanism 10 includes a heat deformable member 34 operatively associated with valve housing 16, valve member 22, and biasing spring 32. In this embodiment, heat deformable member 34 preferably comprises an inexpensively fabricated disposable diaphram which extends between valve member 22 and valve housing 16, with biasing spring 32 held in captive relation to a predetermined loading between housing 16 and deformable member 34 on stem portion 24.

Significantly, deformable member 34 preferably comprises a material which exhibits a tendency to creep at the elevated temperatures of a steam sterilization process. This property of a material is considered as non-elastic deformation of the material when subjected to stresses below the non-elastic yield stress of the material, at temperatures below the melting point of the material. While virtually all solid materials exhibit some tendency to creep, fabrication of deformable member 34 from a thermoplastic material permits this usually undesirable property of materials to be advantageously exploited in the present invention. While deformable member 34 resists and opposes movement of valve member 22 by the biasing action of spring 32 at non-elevated temperatures, such as room temperature, the member 34 commences to non-elastically deform when the valve mechanism 10 is subjected to an environment of elevated temperatures. Thus, deformable member 34 is suitably fabricated to prevent complete closing of container opening 14 by valve member 22 until a selected and predetermined point in the sterilization process. In this way, the desired communication between the interior and exterior of container 12 is provided for a sufficient period of time to permit ingress and egress of hot steam into and from the container 12 to assure sterilization and complete drying of articles within the container.

As will be appreciated, deformable member 34 may be readily inexpensively fabricated for single use service in the valve mechanism 10. In contrast, other portions of the valve mechanism are intended to be reusable, thereby facilitating economical sterilization of articles.

In this embodiment, deformable member 34 is configured as a diaphram which includes a central strengthened hub portion 35 through which stem portion 24 of valve member 22 extends. Hub portion 35 is firmly supported and restrained between head portion 26 of valve member 22 and a shoulder 36 defined by stem portion 24 of the valve member. Deformable member 34 further includes a dimensionally reinforced peripheral bead or rim portion 40 which is tightly restrained between the upper edge 38 of container shoulder portion 17 and the valve housing 16 to assure that the deformable member 34 is supported and peripherally restrained in the intended fashion. The disc-like deformable member 34 is fabricated to have a predetermined thickness to ensure that it creeps in a predictable manner. While deformable member 34 is illustrated as a diaphram, it will be appreciated that other configurations for the member may also be used.

Deformable member 34 can be suitably fabricated from a wide variety of thermoplastic materials which preferably have relatively low heat distortion temperatures and melting points in a range of approximately 300° F. to 450° F. For example, polypropylene homopolymers, ethylene/propylene copolymers, polyethylene, and other plastic materials can be used.

With reference to FIGS. 2-4, the operation of valve operating mechanism 10 will now be described. While the operation of the valve mechanism will be described in the context of use of the valve on the sterilization container, where the valve mechanism is subjected to elevated temperatures in the course of the steam sterilization process, a temperature responsive operating mechanism in accordance with the teachings herein may be readily used in a wide variety of applications where similar temperature responsive operation of an operating member is desired.

By way of example, it has been found that a polypropylene homopolymer conforming to ASTM Specification D2146-Type 1 69017 is one material from which the heat deformable member 34 can be suitably fabricated when the valve mechanism 10 is used for steam sterilization of articles at approximately 270° F. Such a polymer has a heat deflection temperature of 140° F. at 264 pounds per square inch (psi), and 235° F. at 66 psi when tested in accordance with ASTM D648. A polypropylene homopolymer meeting this specification has a melting point of approximately 340° F. Heat deformable member 34 may be configured as a diaphram having a two-inch diameter, having a thickness of 0.050 inches. When deformable member 34 is so configured, it has been found to deform or bow by approximately 0.185 inches in 20 minutes, and 0.266 inches in 40 minutes, when subjected to an elevated temperature of 270° F. and a spring force of 2.85 pounds applied to the center of the diaphram. If the distance between the head portion 26 of valve member 22 and the valve seat 13 which defines container opening 14 is set at approximately 0.250 inches at ambient (room) temperature, valve mechanism 10 will respond to an elevated sterilization temperature of 270° F. by closing slowly, and will not completely close the container opening until between 35 and 40 minutes after the start of the high temperature sterilization cycles. Since it is required that communication between the interior and exterior of the sterilization container 12 be provided for a period exceeding seven minutes to provide adequate steam sterilization of the articles within the container, this configunism is fitted. For example, if opening 14 is relatively small, such as having a diameter of approximately 0.75 inches, the force exerted on valve member 22 by atmospheric pressure (approximately 14.7 psi) acting against the vacuum within the container 12 would be approximately 6.5 pounds. Thus, in such a configuration the force required for unseating valve member 22 to break the seal of the evacuated container 12 is not excessive. However, if a relatively larger container opening 14 is provided, on the order of approximately two inches for example, the force created by the pressure differential between the interior and the exterior of the container on valve member 22 is approximately 46 pounds. Clearly, the force required to break the seal of the container in such a configuration is somewhat excessive to permit ready opening of the container.

Thus, the provision of a venting arrangement on container 12 to permit breaking of its vacuum seal is desirable in some applications. While such a venting arrangement may be readily provided on container 12 apart from valve mechanism 10, FIG. 5 illustrates the incorporation of a suitable selectively operable venting arrangement into valve member 22 of valve mechanism 10. The venting arrangement effects equalization of pressure between the interior and exterior of the sterilization container 12 when the valve member 22 is in its second, closed position. While various configurations of the venting arrangement may be provided, FIG. 5 illustrates the arrangement as including a vent passage 60 defined by and extending the length of valve member 22. The venting arrangement further includes a selectively openable vent needle valve 62 carried by the valve member 22 for selectively opening and closing the vent passage 60. Needle valve 62 would normally be closed during the sterilization process. When access to the contents of container 12 is desired, valve 62 may be opened by unscrewing the valve, thus admitting air into container 12 through the stem and head portions of the valve member 22.

It will be appreciated that such inrushing air would not be sterile, and could contain potentially contaminating particulate matter that would be directed against the sterilized contents of the container as air enters the evacuated container. In view of this, a microporous filter 64 is preferably provided in the path of the inrushing air, such as in head portion 26 of valve member 22 as illustrated. Such a filter can effectively filter out 99.7 percent of all particles greater in size that 0.3 microns. As noted, such a venting arrangement may be provided on container 12 apart from valve mechanism 10, although its incorporation into the valve mechanism particularly facilitates convenient and efficient sterilization of articles.

As earlier noted, one particularly desirable feature of the present valve mechanism 10 is the reusable nature of most of the elements of valve mechanism. Except for a deformable member 34, the entire valve mechanism assembly may be reused. To this end, the valve mechanism may be refurbished for reuse by merely removing valve housing 16 from shoulder portion 17 of container 12, and thereafter removing valve member 22 from the then-deformed deformable member 34. The deformed member 34 may be economically disposed of, and the valve member 22 reinserted through a new, generally flat, non-deformed member 34. Valve member 22 may then be reinserted through biasing spring 32 and guide portion 28 of housing 16, and the entire valve mechanism again fitted to the shoulder portion 17 of container 12. This is a very significant feature of the present invention since very large numbers of articles are routinely sterilized in a health care facility, with reuse of the valve mechanism easily provided by the insertion of a new, economically fabricated deformable member 34 into the mechanism. If the mechanism is provided with a fusible link, such as pin 50 illustrated in FIG. 2A, this may be easily replaced before the valve mechanism is reused. If the valve mechanism includes a venting arrangement such as illustrated in FIG. 5, the venting arrangement is closed before reuse of the valve mechanism.

With reference now to FIGS. 6-8, an alternate embodiment of the present temperature responsive operating mechanism is disclosed. This embodiment of the present invention will again be described in association with sterilization container 12 having valve seat 13 defining container opening 14, although again the mechanism is readily adaptable to a wide variety of applications.

In this embodiment of the present invention, the last two digits of the reference numerals shown in FIGS. 6-8 generally correspond to the reference numerals used in describing like elements of the embodiment of the present invention illustrated in FIGS. 2-4.

As shown in FIG. 6, the temperature responsive valve operating mechanism 110 includes a support structure 116 which is adapted to be suitably mounted on sterilization container 12. The support structure 116 includes an upstanding support strut 118 upon which is pivotally mounted a generally horizontally disposed operating lever 120. A suitable pin 121 operatively connects the operating lever with support strut 118 of support structure 116 to define the fulcrumed portion of the operating level.

Valve mechanism 110 further includes a valve member 122 which is adapted for movement from a first, open position with respect to container opening 14 (FIG. 6), to a second, closed position with respect to the container opening (FIG. 7). Valve mechanism 110 is intended to function in generally the same manner as previously described valve mechanism 10 in that valve member 122 is moved from its first, open position to its second, closed position in response to elevation in the temperature of the environment of the valve mechanism 110, such as during the steam sterilization process.

Operating lever 120 is operatively connected with valve member 122 such as by a suitable slot and pin connection 123 spaced from the lever fulcrum. Other suitable operative connections can be used. Valve member 122 includes an elongate stem portion 124, a portion of which is operatively connected to lever 120, and a head portion 126 connected with the stem portion 124. The valve member 122 is supported by support structure 116 for recriprocable movement with respect thereto by a guide portion 128 which engages stem portion 124 of the valve member and guides its movement. Head portion 126 of the valve member is preferably provided with a suitable elastomeric sealing head gasket 130 adapted to sealingly engage valve seat 13 to seal and close container opening 14 when the valve member 122 is in its second, closed position.

In order to provide the desired operation of valve member 122, valve mechanism 110 includes a biasing spring 132 and a heat deformable member 134 each operatively associated with support structure 116, operating lever 120, and valve member 122. In this illustrated embodiment, biasing spring 132 comprises a tenration of the valve mechanism easily meets this requirement.

Thus, when the valve mechanism 10 is subjected to elevated temperatures such as during sterilization, heat deformable member 34 cooperates with biasing spring 32 to permit controlled and restrained movement of valve member 22 by the biasing spring from its first, opened position illustrated in FIG. 2, to its second, closed position illustrated in FIG. 3. In the closed position of valve member 22, sealing head gasket 30 provided on head portion 26 of the valve member tightly seals against the valve seat 13 of container 12, with deformable member 34 having deformed or distorted from its original, generally flat configuration (FIG. 2) to its deformed or bowed configuration (FIG. 3). Rim portion 40 of deformable member 34 is firmly restrained so that the member deforms in the intended manner. As will be noted, stem portion 24 of valve member 22 is preferably configured with respect to valve housing 16 so that a significant portion of the stem portion extends above guide portion 28 of the housing when the valve member is in its first, open position (FIG. 2), with the end of the stem portion being generally flush with guide portion 28 when the valve member is in its second, closed position (FIG. 3). Thus, a clear visual indication of the position of the valve member is provided to facilitate efficient use of the valve mechanism. In this way, unintended reuse of a valve mechanism which has not been refitted with a non-deformed member 34 is avoided.

As is will be appreciated, the point in time at which valve member 22 moves into its fully closed position during the steam sterilization process may be readily selected by appropriately dimensioning the elements of the valve mechanism. The mechanism preferably functions to completely close the container opening at a point during the vacuum drying cycle of the sterilization process. However, it must be kept in mind that the valve mechanism must function to permit complete vacuum drying of the articles in sterilization container 12, with the valve mechanism preferably thereafter sealing the evacuated container against contamination so that the entire container and its contents may be readily handled and stored after sterilization. FIG. 4 illustrates one unique feature of the present operating mechanism which permits evacuation and subsequent sealing of the sterilization container. Specifically, valve mechanism 10 is capable of functioning in the nature of a one-way valve responsively to a pressure differential between the interior and exterior of sterilization container 12. This is possible because the nature of the valve mechanism is such that deformable member 34 can deform to permit movement of valve member 22 from its second, closed position toward its first, open position against the action of biasing spring 32. This action is possible even at non-elevated temperatures.

Thus, FIG. 4 illustrates this action of the valve mechanism in response to the vapor pressure differential typically created between the interior and exterior of container 12 during the vacuum drying cycle of the sterilization process. Vapor from within the sterilization container can be drawn through container opening 14 via passages 20 and 21, even after valve member 22 has been moved to its second, closed position by biasing spring 32. This unique action of the present valve mechanism greatly facilitates proper sterilization of articles within container 12, since the mechanism does not require any type of separate one-way valving arrangement to permit escape of vapor pressure from within the sterilization container during the vacuum drying cycle of the sterilization process. Thus, adequate drying of the contents of sterilization container 12 during the vacuum drying cycle is assured. When the pressure within the sterilization container is equalized with the pressure exterior of the container (i.e. within the sterilization chamber), valve mechanism 10 functions to tightly reseat valve member 22 in its second, closed position with respect to the container opening to provide a secure, contaminant-proof seal of the evacuated container. When the vacuum of the sterilization chamber is broken, biasing spring 32, together with the pressure differential acting upon valve member 22, assures that the container 12 remains tightly sealed until the contents therein are ready for use.

FIG. 2A illustrates a modification of the valve mechanism 10 illustrated in FIGS. 2–4 which may be desirable for some applications of the valve mechanism. In some steam sterilization processes, a so-called preconditioning cycle is provided during which a cycle of vacuum pulses are alternated with admission of hot steam into the sterilization chamber. In this way, articles within the sterilization container are uniformly wetted with water droplets as their temperature is progressively raised prior to the steam sterilization cycle of the process. Temperature elevation during such a preconditioning cycle invariably falls short of the temperature required for proper sterilization of the contents of the container, although the temperatures obtained may be sufficiently high to result in deformation of deformable member 34, thus commencing unintended and premature closing of container opening 14.

In order to ensure that deformable member 34 does not creep undesirably during such a preconditioning cycle, and that operation of the valve mechanism is initiated or triggered by attainment of a temperature close to that required for sterilization, a suitable fusible link, such as eutectic pin 50 illustrated in FIG. 2A, may be provided for releasably connecting the stem portion 24 of valve member 22 with guide portion 28 of valve housing 16. Pin 50 can be suitably fabricated from a eutectic metal having a melting point close to, or actually at, the requisite sterilization temperature. Alternately, a thermoplastic alloy may be used for fabrication of the pin 50. Other materials can also be used. In this way, movement of valve member 22 by biasing spring 32 is prevented below a predetermined elevated temperature. After such a predetermined temperature is reached within the sterilization chamber, pin 50 will melt or otherwise deform to permit closing of container opening 14 by valve member 22 in an predictable and repeatable fashion. As will be appreciated, the configuration of the releasable connection provided by pin 50 shown in FIG. 2A is intended as merely illustrative, since many other arrangements may also be used for preventing movement of the valve member 22 below a predetermined temperature.

A further modification of the valve mechanism 10 illustrated in FIGS. 2–4 is shown in FIG. 5. In this modification, the valve mechanism is provided with a selectively operable venting arrangement to permit venting of the evacuated sterilization container 12 immediately prior to opening of the container for use of the sterilized articles therein. Provision of such a venting arrangement is desirable for some applications of the present valve mechanism, depending upon the size of the container opening 14 about which the valve mechasion spring extending between and operatively connected with operating lever 120 and support structure 116. As will be appreciated, when biasing spring 132 comprises a tension spring, it should be connected to lever 120 on the same side of the fulcrummed portion of the lever as the operative connection 123 of the lever to the valve member 122. Biasing spring 132 acts through operating lever 120 to urge valve member 122 from its first to its second position.

In order to provide the desired, controlled temperature responsive action of the valve mechanism 110, heat deformable member 134 extends between and is operatively connected with support structure 116 and operating lever 120. In the embodiment illustrated, it is intended that deformable member 134 deform or creep by elongation in response to the stress to which it is subjected by the action of biasing spring 132 through operating lever 120. In such an arrangement, operating lever 120 should be fulcrummed for pivotable movement on support strut 118 at a portion of the lever intermediate the connections of deformable member 134 and biasing spring 132 to the lever (i.e., the connection of member 134 to lever 120 is opposite the connection of spring 132 to lever 120 with respect to the lever fulcrum). However, it will be appreciated that the exact positioning of biasing spring 132 and deformable member 134 with respect to the fulcrummed operating lever 120 and the valve member 122 can be varied while still providing the desired controlled closing of container opening 14 in response to deformation of the deformable member when the valve mechanism 110 is subjected to elevated temperature.

As shown, deformable member 134 is suitably connected with support structure 116 at connection 136, and connected with operating lever at connection 138. Deformable member 134 may be suitably fabricated from a polypropylene homopolymer as described for fabrication of deformable member 34 shown in previously described valve mechanism 10, although again a wide variety of materials may be used for fabrication of the deformable member. The dimensions and configuration of deformable member 134, as well as other portions of the valve mechanism 110 including biasing spring 132, may be appropriately selected to provide the desired period of time for closing of container opening 14. In this way, the desired communication between the interior and the exterior of sterilization container 12 is provided for the requisite period of time during the steam sterilization process.

The functioning of the valve mechanism 110 illustrated in FIGS. 5–6 is similar to the function of previously described valve mechanism 10. As shown in FIG. 6, the valve member 122 of the mechanism 110 is shown in its first, open position with respect to container opening 14. As the temperature of the environment of the valve mechanism 110 elevates, deformable member 134 non-elastically deforms and elongates by the action of biasing spring 132 so that valve member 122 is progressively moved to its second, closed position with respect to container opening 14 (FIG. 7). In this position of the valve member, head gasket 130 provided on head portion 126 firmly seals the container opening 14 to provide a air tight seal thereabout.

FIG. 8 illustrates the unique one-way operation of the valve mechanism 110 in response to the vapor pressure differential which typically exists between the interior of container 12 and of its exterior during the vacuum drying cycle of the sterilization process. As will be noted in FIG. 8, deformable member 134 is illustrated as slightly bowed as valve member 122 is moved from its second closed position toward its first position in opposition to the action of biasing spring 132. Thus, adequate drying of the contents of container 12, and evacuation of the container is assured. When the pressure within container 12 is equalized with the pressure about the exterior of the container, biasing spring 132 acts to again re-seat the valve member 122 with respect to container opening 14.

When the sterilization process is complete and air is admitted to the sterilization chamber, atmospheric pressure acting on the valve member 122 tightly seals the evacuated container 12. The container may be easily handled and stored while its contents remain sterile. When it is desired to break the seal of the container 12, valve member 122 may be lifted to break the seal of the container and permit it to be easily opened. Alternately, a suitable venting arrangement may be provided for breaking the vacuum seal of the container, either incorporated into the valve member 122 as illustrated in previously described FIG. 5, or by providing a suitable venting arrangement on the container 12 apart from the valve mechanism 110. When the valve mechanism 110 is to be used in a steam sterilization unit which includes a preconditioning cycle as described, a suitable fusible link such as pin 50 illustrated in FIG. 2A may be provided for preventing movement of valve member 122 below a predetermined elevated temperature.

Like previously described valve mechanism 10, valve mechanism 110 is intended to be readily reusable by merely replacing the deformed and elongated deformable member 134 with a new, non-deformed member.

While each of the above embodiments has been described as including a heat deformable member which comprises material which creeps to provide the desired function of the mechanism, this action of the deformable member can be varied by appropriately selecting the material and configuration of the deformable member. For example, the heat deformable member (designated 34 and 134, respectively, in the illustrated embodiments) may be provided so that it only initially creeps to permit progressive partial movement of the valve member toward its closed position. Such a deformable member would thereafter reach its non-elastic yield point, whereupon the valve member would no longer be restrained and immediately move to its fully closed position. Of course, the mechanism would still provide the desired one-way valve action, which is particularly important when the mechanism is used in association with the sterilization container.

Thus, the present invention provides a highly unique temperature responsive operating mechanism which is particularly suited for embodiment as a valve operating mechanism for use in association with a sterilization container. When used with such a container, the mechanism functions to slowly close its valve operating member so that communication between the interior and exterior of the sterilization container is provided for a substantial portion of the sterilization process. The material and configuration of the temperature responsive heat deformable member of the mechanism, as well as the biasing spring of the mechanism, can be appropriately selected so that the combination provides the mechanism with an almost unlimited number of operational characteristics. The heat deformable member of the mechanism is preferably fabricated from a thermoplastic material since such materials may be economically and readily fabricated, such as by injection molding, to permit their economical disposal after a single use. While other portions of the mechanism may be also be readily economically fabricated, they are preferably adapted for reuse so that a single mechanism may be used many times by merely refitting it with a new heat deformable member prior to each use. Highly predictable and repeatable operation of the mechanism is readily achieved by the nature of the construction, thus assuring proper sterilization of medical articles and the like when the present operating mechanism is used in association with a sterilization container.

From the foregoing, it will be observed that numerous variations and modifications may be effected without departing from the true spirit and scope of the novel concept of the present invention. It will be understood that no limitatation with respect to the specific embodiments illustrated herein is intended or should be inflicted. It is, of course, intended to cover by the appended claims all such modifications as fall within the scope of the claims.

What is claimed is:

1. A temperature responsive operating mechanism, comprising:
    an operating member movable from a first position to a second position; and
    temperature responsive operating means for moving said operating member from said first position to said second position responsively to elevation in the temperature of the environment of the operating mechanism;
    said operating means comprising biasing means operatively associated with said operating member for urging said operating member from said first position to said second position, and heat deformable means operatively associated with said biasing means and operating member for opposing the biasing action of said biasing means on said operating member, said heat deformable means deforming in response to elevated temperatures below the melting point of the material of the heat deformable means whereby said biasing means gradually moves said operating member from said first position to said second position over a selected period of time;
    said heat deformable means comprising a material which is non-elastically deformable when subjected to stresses by the biasing means below the non-elastic yield stress of the material at elevated temperatures below the melting point of the material.

2. The temperature responsive operating mechanism in accordance with claim 1, wherein:
    said heat deformable means is deformable to permit movement of said operating member from said second position toward said first position in opposition to said biasing means.

3. The temperature responsive operating mechanism in accordance with claim 1, including:
    means for preventing movement of said operating member by said biasing means below a predetermined temperature.

4. The temperature responsive operating mechanism in accordance with claim 1, including:
    a housing within which said operating member is reciprocably disposed, said heat deformable means extending between said operating member and said housing, and said biasing means reacting against said housing for moving said operating member.

5. The temperature responsive operating mechanism in accordance with claim 4, wherein:
    said operating member includes an elongate stem portion; and
    said biasing means comprises compression coil spring means disposed on said stem portion for reaction against said housing;
    said heat deformable means extending between said stem portion and said housing so that said spring means is held in captive relation on said stem portion in a position between said housing and said heat deformable means.

6. The temperature responsive operating mechanism in accordance with claim 1, including:
    a support structure which supports said operating member for reciprocable movement; and
    lever means pivotally connected to said support structure, said lever means being operatively connected to said operating member;
    said biasing means and said heat deformable means each being connected to and extending between said lever means and said support structure.

7. The temperature responsive operating mechanism in accordance with claim 6, wherein:
    said lever means is fulcrummed for pivotal movement on said support structure at a portion of said lever means intermediate the connections of said heat deformable means and said biasing means to said lever means.

8. The temperature responsive operating mechanism in accordance with claim 7, wherein:
    said biasing means comprise tension spring means connected to said lever means on the same side of the fulcrummed portion of said lever means as the operative connection of said operating member to said lever means.

9. A temperature responsive valve mechanism adapted for use with an associated sterilization container having an opening providing communication between the interior and exterior of the container, said valve mechanism comprising:
    support means adapted for mounting on a container,
    a valve operating member supported by said support means for movement between a first, opened position wherein said opening is unsealed, and a second, closed position wherein said valve member closes and seals the container opening;
    biasing means operatively associated with said support means and said valve member for urging said valve member from said first position toward said second position; and
    heat deformable means operatively associated with said support means, said biasing means, and said valve member, said heat deformable means being arranged to oppose the biasing action of said biasing means on said valve member to prevent movement of said valve member to said second position until said valve mechanism is subjected to elevated temperatures, said heat deformable means deforming at elevated temperatures below the melting point of the material of the heat deformable means to permit gradual movement of said valve member to said second position by said biasing means.

10. The temperature responsive valve mechanism in accordance with claim 9, wherein:

said heat deformable means comprises a material which is non-elastically plastically deformable without rupture when subjected to stresses by said biasing means below the non-elastic yield stress of the material at elevated temperatures below the melting point of the material.

11. The temperature responsive valve mechanism in accordance with claim 9 or 10, wherein
said heat deformable means is deformable to permit movement of said valve member from said second position toward said first position in opposition to said biasing means.

12. The temperature responsive mechanism in accordance with claim 9, wherein:
said biasing means and heat deformable means permit movement of said valve member from said second position toward said first position responsively to a pressure differential between the interior and exterior of the container.

13. The temperture responsive mechanism in accordance with claim 9, including:
fusible means releasably connecting said valve member and support means for preventing movement of said valve member by said biasing means below a predetermined temperature.

14. The temperature responsive valve mechanism in accordance with claim 9, including:
selectively operable vent means for effecting equilization of pressure between the interior and exterior of the container when said valve member is in the second, closed position.

15. The temperature responsive mechanism in accordance with claim 9, wherein:
said support means comprises a housing within which said valve member is reciprocably disposed, said housing being adapted for mounting about the container opening and defining at least one passage accommodating communication between the interior and exterior of the container via the container opening and said passage.

16. The temperature responsive mechanism in accordance with claim 15, wherein:
said valve member includes a head portion adapted to sealingly close the container opening and a stem portion connected to said head portion, said stem portion engaging said housing for guiding the movement of said valve member with respect to said housing.

17. The temperature responsive valve mechanism in accordance with claim 16, wherein:
said heat deformable means comprises a heat deformable member extending between and connected to said valve member and said housing, said biasing means comprising spring means held captive on said stem portion in a position between said housing and said heat deformable member.

18. The temperature responsive valve mechanism in accordance with claim 17, wherein:
said spring means comprises a compression coil spring disposed about said stem portion of said valve member.

19. The temperature responsive valve mechanism in accordance with claim 16, including:
selectively operable vent means for effecting equilization of pressure between the interior and exterior of the container when said valve member is in the second, closed position;
said vent means including a vent passage defined by said valve member, and a vent valve carried by said valve member for selectively opening and closing said vent passage.

20. The temperature responsive valve mechanism in accordance with claim 19, including:
filter means mounted on said valve member in association with said vent passage for filtering air passing through said vent passage.

21. The temperature responsive valve mechanism in accordance with claim 9, wherein:
said support means supports said valve member for reciprocable movement and comprises a support structure engaging said valve member; and
lever means pivotally mounted on said support structure having a portion operatively connected to said valve member;
said heat deformable means and said biasing means each being operatively connected with and extending between said lever means and said support structure.

22. The temperature responsive valve mechanism in accordance with claim 21, wherein;
said lever means includes a portion fulcrummed to said support structure intermediate the operative connection of said heat deformable member to said lever means and the operative connection of said biasing means to said lever means.

23. The temperature responsive valve mechanism in accordance with claim 22, wherein:
said biasing spring means comprises a tension spring operatively connected to said lever means on the same side of the fulcrummed portion of said lever means as the operative connection of said valve member to said lever means.

24. The temperature responsive valve mechanism in accordance with claim 23, wherein:
said heat deformable means comprises a heat deformable member operatively connected to said lever means on the side of the fulcrummed portion of said lever means opposite the connection of said spring means to said lever means, said heat deformable member thereby being arranged to deform by elongation during movement of said valve member from said first to said second position.

25. A temperature responsive valve mechanism adapted for use with an associated sterilization container having an opening providing communication between the interior and exterior of the container, said valve mechanism comprising:
a valve housing adapted to be fitted to a container about the container opening, said housing defining at least one passage accommodating communication between the interior and exterior of the container via said opening and said passage;
a valve member reciprocably disposed within said housing and including a stem portion engaging said housing for guiding the movement of said valve member, and further including a head portion adapted to sealingly engage the container for closing the container opening, said valve member being movable from a first position wherein the container opening is unsealed, to a second position wherein said valve member closes and seals the container opening;
a heat deformable member extending between said valve member and said housing; and spring means disposed about said stem portion in captive relation between said heat deformable member and said housing, said spring means urging said valve member from said first position toward said second position;

said heat deformable member being arranged to oppose the action of said spring means on said valve member whereby said heat deformable member plastically deforms in response to elevated temperature below the melting point of the material of the heat deformable member to permit gradual movement of said valve member from said first position to said second position.

26. A temperature responsive valve mechanism adapted for use with an associated sterilization container defining an opening adapted to provide communication between the interior and exterior of the container, said valve mechanism comprising:

- a support structure adapted to be fitted to a sterilization container;
- a valve member reciprocably mounted in said support structure for movement between a first position wherein the container opening is unsealed, and a second position wherein said valve member closes and seals the container opening;
- a lever pivotally mounted on said support structure including a portion operatively connected to said valve member spaced from the fulcrum of said lever;
- tension spring means connected to and extending between said lever and said support structure, said spring means being connected to said lever on the same side of the lever fulcrum as the operative connection of said lever to said valve member, said spring means acting through said lever to urge said valve member from said first position toward said second position; and
- a heat deformable member connected to extending between said support structure and said lever, said deformable member being connected to said lever on the side of the lever fulcrum opposite the connection of said spring means to said lever, said deformable member opposing movement of said valve member into said second position until the valve mechanism is subjected to elevated temperatures below the melting point of the material of the heat deformable member whereupon the deformable member elongates and thereby permits gradual movement of said valve member from said first position into said second position.

* * * * *